United States Patent

Van Der Puy et al.

Patent Number: 5,086,190
Date of Patent: Feb. 4, 1992

[54] METHOD OF FLUORINATING BY USING N-FLUOROPYRIDINIUM PYRIDINE HEPTAFLUORODIBORATE

[75] Inventors: Michael Van Der Puy, Cheektowaga; David Nalewajek, West Seneca; George A. Shia, North Tonawanda; William J. Wagner, Hamburg, all of N.Y.

[73] Assignee: Allied-Signal Inc., Morris Township, Morris County, N.J.

[21] Appl. No.: 647,101

[22] Filed: Jan. 29, 1991

Related U.S. Application Data

[60] Continuation-in-part of Ser. No. 497,382, Mar. 21, 1990, abandoned, which is a division of Ser. No. 406,659, Sep. 13, 1989, Pat. No. 4,935,519, which is a continuation-in-part of Ser. No. 351,115, May 12, 1989, abandoned.

[51] Int. Cl.$^5$ ............................................ C07J 75/00
[52] U.S. Cl. .................................. 552/521; 552/610; 552/623
[58] Field of Search ..................... 552/610, 623, 521

[56] References Cited

U.S. PATENT DOCUMENTS 4,935,519  6/1990  Van Der Puy et al. .............. 546/13

*Primary Examiner*—Howard T. Mars
*Assistant Examiner*—Kimberly J. Kestler
*Attorney, Agent, or Firm*—Melanie L. Brown; Jay P. Friedenson

[57] ABSTRACT

The present invention provides a novel compound represented as

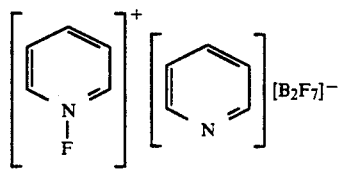

The present novel compound is prepared by reacting fluorine with pyridine-boron trifluoride and is useful as a fluorinating agent in the fluorination of organic compounds.

7 Claims, No Drawings

METHOD OF FLUORINATING BY USING N-FLUOROPYRIDINIUM PYRIDINE HEPTAFLUORODIBORATE

BACKGROUND OF THE INVENTION

This application is a continuation-in-part application of Ser. No. 497,382 filed Mar. 21, 1990, abandoned, which is divisional application of Ser. No. 406,659 filed Sept. 13, 1989, now U.S. Pat. No. 4,935,519 which is a continuation-in-part application of Ser. No. 351,115 filed May 12, 1989, abandoned.

This invention relates to N-fluoropyridinium pyridine heptafluorodiborate.

Many fluorinating reagents are known in the art. One type of fluorinating reagent is known as electrophilic fluorinating reagents. This type of fluorinating reagent is characterized by a structure containing an O-F or N-F bond. Electrophilic fluorinating reagents having an N-F bond include 1-fluoro-2-pyridone as taught by S. T. Purrington et al., "1-Fluoro-2-pyridone: A Useful Fluorinating Reagent", *J. Org. Chem.* 48, 761 (1983); N-fluoro-N-alkylsulfonamides as taught by W. E. Barnette, "N-Fluoro-N-alkylsulfonamides: Useful Reagents for the Fluorination of Carbanions", *J. Am. Chem. Soc.* 106, 452 (1984); N-fluoroquinuclidinium fluoride as taught by R. E. Banks et al., "Electrophilic Fluorination with N-fluoroquinuclidinium Fluoride", *J. of Fluorine Chem.* 32, 461 (1986); and N-fluoropyridinium salts as taught by T. Umemoto et al., "N-fluoropyridinium Triflate and its Analogs, The First Stable 1:1 Salts of Pyridine Nucleus and Halogen Atom", *Tetrahedron Letters* 27(28), 3271 (1986).

N-fluoropyridinium salts have been shown to be stable fluorinating reagents with the ability to fluorinate a variety of organic compounds. For example, T Umemoto et al., "N-fluoropyridinium Triflate and Its Derivatives: Useful Fluorinating Agents", *Tetrahedron Letters* 27(37), 4465 (1986) report that these salts are useful in the fluorination of aromatic compounds and the conversion of enol silyl ethers to alpha-fluoroketones. T. Umemoto et al., "Base-Initiated Reactions of N-fluoropyridinium Salts; A Novel Cyclic Carbene Proposed as a Reactive Species", *Tetrahedron Letters* 28(24), 2705 (1987) report that N-fluoropyridinium salts can also be converted into useful pyridine derivatives such as 2-chloropyridine.

However, N-fluoropyridinium salts are disadvantageous because the current method for their preparation is hazardous. As taught by the aforementioned first Umemoto et al. article, fluorine is first reacted with pyridine or a substituted pyridine at low temperature to give a pyridine difluoride. In a second step, the pyridine difluoride is converted into an N-fluoropyridinium salt. N-fluoropyridinium tetrafluoroborate and its method of preparation are shown below:

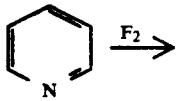

-continued

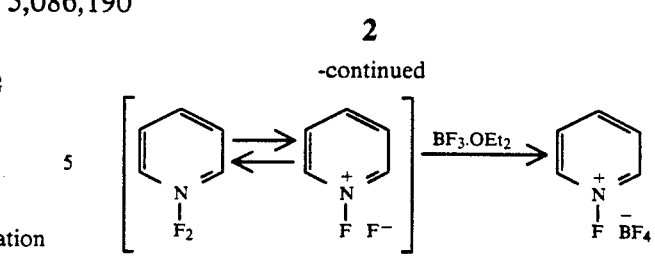

See also European Patent Application Publication 204,535. As those skilled in the art know, pyridine difluorides are inherently unstable and have been known to decompose violently even at temperatures below 0° C. If the foregoing preparation method were used on a large scale, the formation of pyridine difluoride, even if temporary, would be extremely hazardous In response to the foregoing hazard, we attempted to prepare N-fluoropyridinium tetrafluoroborate without the formation of isolable quantities of pyridine difluoride by reacting fluorine with pyridine-boron trifluoride complex. The resulting product was totally unexpected.

SUMMARY OF THE INVENTION

The resulting product is a novel compound represented as

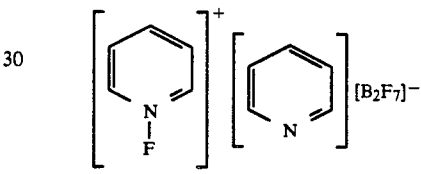

This novel compound will be referred to as N-fluoropyridinium pyridine heptafluorodiborate. In contrast to the N-fluoropyridinium tetrafluoroborate taught by the aforementioned first Umemoto et al. article, the present compound has an additional pyridine ring therein and a heptafluorodiborate group rather than a tetrafluoroborate group. Also, Umemoto et al. report that N-fluoropyridinium tetrafluoroborate has a melting point of 90°-91° C. while the present novel compound has a melting point of 196°-197° C.

The present compound is useful as a fluorinating agent and is less expensive than the currently used fluorinating agent, N-fluoropyridinium triflate. Other advantages of the present compound are that the preparation hazards associated with pyridine difluoride intermediates are eliminated and the present compound can be prepared at more convenient temperatures.

It should be noted that during our attempt to prepare N-fluoropyridinium tetrafluoroborate based salts without the formation of isolable quantities of pyridine difluoride, we reacted fluorine with 3,5-dichloropyridine-boron trifluoride complex. As expected based on the teachings of the aforementioned Umemoto et al. article, 3,5-dichloro-N-fluoropyridinium tetrafluoroborate formed as shown in Example 45 of the aforementioned European Patent Application; a chlorinated version of the present compound did not form. This further demonstrates the unexpectedness of the present N-fluoropyridinium pyridine heptafluorodiborate.

Other advantages of the present invention will become apparent from the following description and appended claims.

DETAILED DESCRIPTION OF THE PREFERRED EMBODIMENTS

The present N-fluoropyridinium pyridine heptafluorodiborate is prepared by reacting fluorine with pyridine-boron trifluoride dissolved in a solvent at a temperature of about −40° to about +35° C. Commercially available pyridine-boron trifluoride may be used to prepare the present compound or pyridine-boron trifluoride complex may be prepared by simply passing $BF_3$ over pyridine.

A solvent which will dissolve appreciable amounts of pyridine-boron trifluoride, is inert to fluorine, and is unreactive towards the product is useful herein. An example of a useful solvent is acetonitrile. Preferably, the solvent is commercially available acetonitrile.

Preferably, the dissolved pyridine-boron trifluoride is at a temperature of about −25° to about +25° C., and more preferably, about −5° to about +25° C.

Commercially available fluorine is then bubbled into the solution. For safety reasons, it is advantageous to dilute the fluorine with commercially available nitrogen. Based on the amount of nitrogen used, the amount of fluorine used may be about 5 to 35 percent by volume and more specifically, about 10 to 20 percent by volume. Typically, about 1 mole equivalent of fluorine is added to the pyridine-boron trifluoride in acetonitrile. Adding more than 1 mole equivalent of fluorine wastes the fluorine while adding less then 1 mole equivalent of fluorine wastes the pyridine-boron trifluoride.

As reported in present Example 1, seven grams of pyridine-boron trifluoride were dissolved in 50 ml acetonitrile and reacted with fluorine to give a product yield of 66%. We then found that upon scale-up, the use of larger quantities of pyridine-boron trifluoride resulted in poorer yields.

We then accidently found that product yields are unexpectedly improved by running the present reaction in the presence of water. Because commercially available solvent may have water therein, the solvent may serve as a source of water. For example, one sample of commercially available acetonitrile contained 0.22% water by weight or about 170 microliters of water in 100 cc of acetonitrile. Another sample of commercially available acetonitrile contained 0.005% by weight or about 4 microliters of water in 100 cc of acetonitrile. If the solvent contains insufficient water or does not contain any water, water will then have to be added in order to arrive at the total amount of water required as described below.

As such, preferably the fluorine is reacted with the pyridine-boron trifluoride dissolved in solvent in the presence of water. Preferably the total amount of water present is about 2 to about 12 microliters per gram of starting pyridine-boron trifluoride. The use of greater than about 20 microliters of water per gram of starting pyridine-boron trifluoride causes the precipitation of pyridinium tetrafluoroborate salt which does not lead to the desired product and also contaminates the desired product. More preferably, the total amount of water present is about 3 to about 8 microliters per gram of starting pyridine-boron trifluoride, and most preferably, about 4 to about 6 microliters per gram.

The water may be added to the reaction mixture in several different ways. For example, the water may be added to the pyridine-boron trifluoride dissolved in solvent prior to reaction with the fluorine; this method of water addition is undesirable because precipitation of the pyridinium tetrafluoroborate salt may occur. As another example, a stream of nitrogen or air may be bubbled through water and then the wet gas may be passed into the reactor to continuously supply a steady but very low supply of water; the flow rate of the wet gas is adjusted to supply the required amount of water based on the starting pyridine-boron trifluoride in the reactor and the reaction rate as dictated by the fluorine mass flow rate. In another method which is preferred, the water is incrementally added to the reaction mixture and the rate of the incremental water addition is determined by the fluorine mass flow rate; such incremental additions may be done continuously or intermittently. Most preferably, the amount of each incremental addition is about 0.3 to about 2.0 microliters of water per gram of starting pyridine-boron trifluoride.

We have also found that the N-fluoropyridinium pyridine heptafluorodiborate product is less soluble than pyridine-boron trifluoride in acetonitrile. If the ratio of pyridine-boron trifluoride to acetonitrile is too great, the product comes out of solution and interferes with the fluorine flow and thus the reaction. Preferably, the ratio of grams of pyridine-boron trifluoride to cc of acetonitrile does not exceed 0.8.

The fluorine uptake may be conveniently monitored by passing the gas effluent from the reactor through a bubbler containing a solution of potassium iodide in water. If the fluorine uptake ceases, the fluorine passes through the reactor and immediately reacts with the potassium iodide in the bubbler liberating iodine which turns the almost colorless solution a dark brown.

The N-fluoropyridinium pyridine heptafluorodiborate is useful as a fluorinating agent. This compound is useful in fluorinating organic compounds including aliphatic compounds such as 1-octyl magnesium bromide and enolate derivatives such as 3-pentanone enol acetate; alicyclic compounds such as 1-morpholino-1-cyclohexene, 1-morpholino-1-cyclopentene, 2-carboethoxy cyclopentanone and cyclohexanone trimethyl silyl enol ether; and aromatic compounds such as benzene and anisole.

Activated olefins of Formula (I) below can be fluorinated

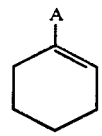

or Formula (II)

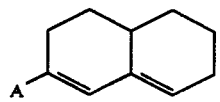

wherein A is selected from the group consisting of —OCOR, —OR, —OSiR$_3$, —NCOR, and NR$_2$ wherein R is an alkyl group having 1 to 6 carbon atoms. Examples of activated olefins are set forth in Table 1 below. In Table 1, F(I) means Formula (I) and F(II) means Formula (II).

TABLE I

| F(I) | F(II) | A | Name |
|---|---|---|---|
| X | — | —OCOCH$_3$ | 1-acetoxy-1-cyclohexene |

TABLE I-continued

| F(I) | F(II) | A | Name |
|---|---|---|---|
| X | — | —OCH$_3$ | 1-methoxy-1-cyclohexene |
| X | — | —OSi(CH$_3$)$_3$ | 1-cyclohexenyloxy-trimethylsilane |
| X | — | —NCOCH$_3$ | 1-acetamino-1-cyclohexene |
| X | — | —N—C$_4$H$_8$  | 1-pyrrolidino-1-cyclohexene |
| — | X | —OCOCH$_3$ | 6-acetoxy-1,2,3,7,8,8a-hexahydronaphthalene |
| — | X | —OCH$_3$ | 1,2,3,7,8,8a-hexahydro-6-methoxynaphthalene |
| — | X | —OSi(CH$_3$)$_3$ | 1,2,3,7,8,8a-hexahydro-6-trimethyloxysilylnaphthalene |
| — | X | —NCOCH$_3$ | 6-acetamino-1,2,3,7,8,8a-hexahydronaphthalene |
| — | X | —N—C$_4$H$_8$ | 1,2,3,7,8,8a-hexahydro-6-pyrrolidinonaphthalene |

Organic sulfides which can be fluorinated are represented by Formula (III)

RSCH$_2$R' wherein R is selected from the group consisting of an alkyl group having 1 to 6 carbon atoms and an aryl group having 6 to 10 carbon atoms and R' is selected from the group consisting of hydrogen, an alkyl group having 1 to 6 carbon atoms, an ester group having 2 to 7 carbon atoms, and a ketone having 2 to 7 carbon atoms.

When an activated olefin of the Formula (I) above is being fluorinated, the fluorine adds to the 2-position of the ring. Although not wishing to be bound by theory, we believe that the fluorine adds to the ring by a one-electron transfer mechanism as taught by Umemoto et al.

When an activated olefin of the Formula (II) above is being fluorinated, the fluorine adds to the 4-position of the ring. Although not wishing to be bound by theory, we believe that the fluorine adds to the ring by one-electron transfer mechanism as taught by Umemoto et al.

When a sulfide of the Formula (III) is being fluorinated, the fluorine replaces one of the hydrogens adjacent to the sulfur atom. Although not wishing to be bound by theory, we believe that alpha-fluorination of sulfides occurs via oxidative fluorination of the sulfur followed by rearrangement of fluorine to the alpha-carbon.

Fluorinated aliphatic compounds are useful in many applications including pharmaceuticals while fluorinated aromatic compounds are useful in many applications including chemical intermediates for pharmaceutical and agricultural compounds.

As such, the present invention provides a method of fluorinating organic compounds by using N-fluoropyridinium pyridine heptafluorodiborate as a fluorinating agent. The method of fluorinating an organic compound involves reacting the N-fluoropyridinium pyridine heptafluorodiborate with the organic compound in a solvent at a temperature sufficient to effect the fluorination. Preferably, the solvent is methylene chloride or acetonitrile.

The fluorination temperature is about 0° C. to about 100° C. Preferably, the temperature is about 70° C. to about 90° C. for the fluorination of enol acetates and about 0° C. to about 10° C. for the fluorination of trimethylsilyl enol ethers. Preferably, the temperature is about 15° C. to about 35° C. for the fluorination of the other above-identified activated olefins and sulfides.

The present invention is more fully illustrated by the following non-limiting Examples.

EXAMPLE 1

Example 1 is directed to the preparation of N-fluoropyridinium pyridine heptafluorodiborate.

Pyridine-boron trifluoride complex (7 g, 0 0477 mol) was dissolved in 50 mL acetonitrile at ice bath temperature. Fluorine (8 cc/min) diluted with nitrogen (68 cc/min) was bubbled in for 3 hours (0.054 mol fluorine). After the addition was complete, the solution was triturated with carbon tetrachloride and cooled to give 5.2 g of a peach-colored solid. Recrystallization from acetone gave tan crystals, mp 196°-7° C. Anal. Calcd. for C$_{10}$H$_{10}$B$_2$F$_8$N$_2$: C, 36.20, H, 3.04; N, 8.44; Found: C, 36.75; H, 3.39; N, 8.06. Molecular weight by iodometric titration, Calcd.: 331.6; Found: 323. $^{19}$F NMR: 48.2 downfield from CFCl$_3$ (1 F) and 150.1 ppm upfield from CFCl$_3$ (7 F); $^1$H NMR (CH$_3$CN): 9.24 (dd, 2H), 8.5-8.8 (m, 4H), 7.9-8.4 (m, 4H) ppm; $^{11}$B NMR: $-0.12$ ppm relative to NH$_4$BF$_4$; $^{13}$C NMR 148.8, 148.0, 142.7, 137.3, 131.3 and 128.8 ppm.

Examples 2-9 are directed to the fluorination of various organic compounds by using N-fluoropyridinium pyridine heptafluorodiborate as a fluorinating agent.

EXAMPLE 2

The reagent (0.25 g) from Example 1 and 2 mL benzene were refluxed in 15 mL methylene chloride overnight. The presence of fluorobenzene was indicated by GC-MS.

EXAMPLE 3

Anisole (0.1 g) and 0.25 g of the reagent from Example 1 were refluxed in CH$_2$Cl$_2$. After 7 hours, 20% of the anisole was converted to a 1:1 mixture of 2-fluoro- and 4-fluoroanisole. After 24 hours reflux, the conversion was 70%.

EXAMPLE 4

The fluorinating reagent prepared according to Example 1 (9.95 g, 30 mmol) dissolved in 40 mL dry acetonitrile is added slowly to a solution of 1-morpholino-1-cyclohexene (3.35 g, 20 mmol) in 15 mL acetonitrile at a rate to maintain a temperature of less than 35° C. The mixture is then stirred at room temperature for an additional six hours. Aqueous 2 N HCl (25 mL) is added and the mixture refluxed for one hour. The cooled mixture is diluted with 50 mL water and extracted three times with 35 mL methylene chloride. The combined organic layers are dried (MgSO$_4$) and solvent removed to leave a residue containing 3-fluorocyclohexanone which is purified chromatographically.

EXAMPLES 5-9

The following organic compounds and 0.25 g of the reagent from Example 1 are refluxed in methylene chloride, except for Example 9 where the reaction is carried out at room temperature in tetrahydrofuran, to prepare fluorinated organic compounds.

| Example | Organic Compound |
|---|---|
| 5 | 1-morpholino-1-cyclopentene |

| Example | Organic Compound |
| --- | --- |
| 6 | 2-carboethoxy cyclopentanone |
| 7 | cyclohexanone trimethyl silyl enol ether |
| 8 | 3-pentanone enol acetate |
| 9 | 1-octyl magnesium bromide |

Examples 2-9 show that the reagent fluorinates aromatic and aliphatic compounds.

EXAMPLE 10

This Example provides additional chemical evidence for the existence of an N-fluoropyridium cation in the present compound.

The fluorinating reagent (0.5 g) from Example 1 was refluxed for 1 hour in 5 mL acetonitrile containing 1 g KF. From the reaction mixture, pyridine, 2-fluoropyridine, and 2-acetamidopyridine were identified by GC-MS. The latter two products are consistent with the behavior of N-fluoropyridinium salts as reported by Umemoto et al. "Preparation of 2-Fluoropyridines via Base - Induced Decomposition of N-Fluoropyridinium Salts", J. Org. Chem. 54, 1726 (1989).

COMPARATIVE

This Comparative illustrates the advantage of adding water during the reaction of the fluorine and the pyridine-boron trifluoride in scale-up in improving product yield.

To a reactor, 80.0 g of pyridine-boron trifluoride and 320 ml of acetonitrile were charged and purged with $N_2$. The reactor was placed in an ice-bath and a mixture of 10% $F_2$ in $N_2$(V/V) was bubbled into the stirred solution at a rate of 200 cc/min. After nearly three hours of addition, the exhaust gases from the reaction turned the potassium iodide trap to a dark color which indicated that the reaction was not absorbing $F_2$. The reactor contents were cooled and carbon tetrachloride was added; this addition precipitated white crystals (CROP 1). These crystals were collected and vacuum dried at 25° C. for several hours (melting point: 192°–194° C.). $^1H$ and $^{19}F$-NMR showed the presence of product. To the filtrate from CROP 1 above, more carbon tetrachloride was added which precipitated a second crop(CROP 2) of crystals. These crystals were collected and dried as above to give a solid with a melting point: 194°–197° C. and again $^1H$ and $^{19}F$-NMR showed presence of product. The total yield of CROP 1 and CROP 2 was 24.9%.

EXAMPLE 11

To a reactor, 80.0 g pyridine-boron trifluoride complex and 300 ml of acetonitrile were charged and purged with $N_2$. The reactor was placed in an ice-bath and a mixture of 10% $F_2$ in $N_2$(V/V) was bubbled through the stirred solution at a rate of 200 cc/min. After 2.5 hours, the exhaust gases from the reaction turned potassium iodide solution dark which indicated that $F_2$ was no longer being absorbed. 100 microliters of water were then added and fluorination was resumed with a fresh potassium iodide trap in place. The reaction absorbed $F_2$ for 1.5 hours at which point, the trap darkened. 50 microliters of water were added to the reaction and fluorination was resumed. In 0.5 hour, $F_2$ was no longer being absorbed. Two more additions of 50 microliters of water each were made, each time with subsequent $F_2$ addition and absorption. The reaction liquor was cooled and R-113 added to precipitate near white crystals which were vacuum dried at 25° C. for several hours. For CROP 1, the yield was 47.3 g or 52.4% with a melting point of 192°–194° C. The filtrate was roto-vapped to give a second crop of crystals which were filtered and vacuum dried. The yield was 27.0 g with a melting point of 150°–180° C. $^1H$ and $^{19}F$-NMR verified the product in both CROPS. CROP 2 showed some impurities.

Examples 12 through 18 are directed to the fluorination of various organic compounds by using N-fluoropyridinium pyridine heptafluorodiborate as a fluorinating agent.

EXAMPLE 12

This Example is directed to the fluorination of 3,17beta-diacetoxy-3,5-androstadiene to produce 6-fluorotestosterone acetate.

We prepared 3,17beta-diacetoxy-3,5-androstadiene by using the procedure of Chavis, C.; Mousseron-Canet, M. Bull. Soc. Chim. France (1971), 632.

To a solution of 3,17beta-diacetoxy-3,5-androstadiene (100 milligrams, 0.27 millimole) in acetonitrile (0.6 milliliter) was added N-fluoropyridinium pyridine heptafluorodiborate (98 milligrams, 0.30 millimole) and the reaction stirred at 40° C. for 2 days. The mixture was poured into ether (10 milliliters), filtered through anhydrous $MgSO_4$ and evaporated to afford 90 milligrams (96% yield) of a 1 to 1.1 ratio of 6 alpha- to 6 beta-fluorotestosterone acetate.

EXAMPLE 13

This Example is directed to the fluorination of 3,17beta-bistrimethyl siloxy-3,5androstadiene to produce 6-fluoro-17beta-trimethylsiloxytestosterone.

We prepared 3,17beta-bistrimethylsiloxy-3,5-androstadiene by using the procedure of Paterson, I; Price, L. G. Tetrahedron Letters (1981) 22, 2833.

To a solution of 3,17beta-bistrimethylsiloxy-3,5-androstadiene (150 milligrams, 0.35 millimole) in acetonitrile (1.4 millimeters) was added N-fluoropyridinium pyridine heptafluorodiborate (127 milligrams, 0.38 millimole) and the reaction stirred at room temperature for 18 hours. The mixture was poured into ether (10 milliliters), filtered through anhydrous $MgSO_4$ and evaporated to afford 111 milligrams (88% yield) of a 1 to 3 ratio of 6 alpha- to 6 beta-fluoro-17 beta-trimethylsiloxytesterone.

EXAMPLE 14

This Example is directed to the fluorination of 1-acetoxy-4-t-butylcyclohexene to produce 2-fluoro-4-t-butylcyclohexanone.

We prepared 1-acetoxy-4-t-butylcyclohexene by using the procedure of House, H. O.; Tefertiller, B. A.; Olmstead, H. D. J. Org. Chem. (1968) 33, 935.

To a solution of 1-acetoxy-4-t-butylcyclohexene (1 gram, 5.1 millimoles) in acetonitrile (5 milliliters) was added N-fluoropyridinium pyridine heptafluorodiborate (3.10 grams, 9.4 millimoles) in acetonitrile (10 milliliters) and the reaction refluxed for 18 hours. The mixture was poured into ether (75 milliliters), filtered through anhydrous $MgSO_4$ and evaporated. The residue was chromatographed on silica gel to afford 0.4 gram. (62% yield) of a 2.5 to 1 ratio of cis- to trans-2-fluoro-4-t-butylcyclohexanone.

EXAMPLE 15

This Example is directed to the fluorination of enol-acetate of alpha-tetralone to produce 2-fluoro-alpha-tetralone.

We prepared the enol-acetate of alpha-tetralone according to the procedure of Rozen, S.; Menahem, Y. *J. Fluorine Chem.* (1980) 16, 19.

To a solution of the enol-acetate of alpha-tetralone (1 gram, 5.3 millimoles) in acetonitrile (5.3 milliliters) was added N-fluoropyridinium pyridine heptafluorodiborate (3.53 grams, 10.6 millimoles) in acetonitrile (10 milliliters) and the reaction refluxed for 18 hours. The mixture was poured into ether (75 milliliters), filtered through anhydrous MgSO4 and evaporated. The residue was chromatographed on silica gel to afford 0.53 gram (61% yield) of 2-fluoro-alpha-tetralone.

EXAMPLE 16

This Example is directed to the fluorination of 1-cyclohexenyloxytrimethylsilane to produce 2-fluorocyclohexanone.

We purchased 1-cyclohexenyloxytrimethylsilane from Aldrich Chemical Co.

To a solution of 1-cyclohexenyloxytrimethylsilane (1 gram, 5.9 millimoles) in acetonitrile (6 milliliters) was added N-fluoropyridinium pyridine heptafluorodiborate (2.14 grams, 6.45 millimeters) and the reaction stirred for 1 hour at 0° C. The mixture was poured into ether (75 milliliters), filtered through anhydrous MgSO4 and evaporated. The residue was chromatographed on silica gel to afford 0.25 gram (37% yield) of 2-fluorocyclohexanone.

EXAMPLE 17

This Example is directed to the fluorination of 3 beta-acetoxy-17-acetamino-5,16-androstadiene to produce 16-fluoro-3beta-acetoxy-5-androsten-17-one.

We prepared 3beta-acetoxy-17-acetamino-5,16-androstadiene by using procedure of Rosenkranz, G.; Mancera, O.; Sondheimer, F.; Djerassi, C. *J. Org. Chem.* (1956) 21, 520.

To a solution of 3beta-acetoxy-17-acetamino-5,16-androstadiene (150 milligrams, 0.40 millimole) in acetonitrile (0.8 milliliters) was added N-fluoropyridinium pyridine heptafluorodiborate (150 milligrams, 0.44 millimole) and the reaction stirred at room temperature for 5 days. The mixture was then diluted with 10% HCl (1 milliliter) and stirred for an additional 18 hours. Next, the solution was extracted with ether (3×1 milliliter), the combined organic layers filtered through anhydrous MgSO4 and evaporated to afford 115 milligrams (82% yield) of a 15 to 1 ratio of 16 alpha- to 16 beta-fluoro-3beta-acetoxy-5-androsten-17-one.

EXAMPLE 18

This Example is directed to the fluorination of p-chlorophenyl methyl sulfide to produce fluoromethyl p-chlorophenyl sulfide.

We purchased p-chlorophenyl methyl sulfide from American Tokyo Kasei, Inc.

To a solution of p-chlorophenyl methyl sulfide (100 milligrams, 0.63 millimole) in acetonitrile (1 milliliter) was added N-fluoropyridinium pyridine heptafluorodiborate (210 milligrams, 0.63 millimole) and the reaction stirred at room temperature for 18 hours. The mixture was poured into ether (10 milliliters), filtered through anhydrous MgSO4 and evaporated to afford a mixture of starting material and fluoromethyl p-chlorophenyl sulfide (26% by NMR).

Having described the invention in detail and by reference to preferred embodiments thereof, it will be apparent that modifications and variations are possible without departing from the scope of the invention defined in the appended claims.

What is claimed is:

1. A method of fluorinating an organic selected from the group consisting of 3,17$\beta$-diacetoxy-3,5-androstadiene, 3,17$\beta$-bistrimethylsiloxy-3,5-androstadiene, and 3$\beta$-acetoxy-17-acetamino-5,16-androstadiene compound by reacting a compound represented as

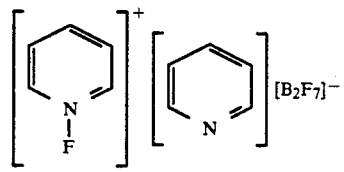

with said organic compound in a solvent at a temperature sufficient to effect said fluorination.

2. The method of claim 1 wherein said solvent is methylene chloride.

3. The method of claim 1 wherein said solvent is acetonitrile.

4. The method of claim 1 wherein said organic compound is 3,17 beta-diacetoxy-3,5-androstadiene.

5. The method of claim 1 wherein said organic compound is 3,17 beta-bistrimethylsiloxy-3,5-androstadiene.

6. The method of claim 1 wherein said organic compound is 3-beta-acetoxy-17-acetamino-5,16-androstadiene.

7. The method of claim 1 wherein said fluorination temperature is about 0° C. to about 100° C.

* * * * *

UNITED STATES PATENT AND TRADEMARK OFFICE
CERTIFICATE OF CORRECTION

PATENT NO. : 5,086,190

DATED : February 4, 1992

INVENTOR(S) : Michael Van Der Puy, et. al.

It is certified that error appears in the above-identified patent and that said Letters Patent is hereby corrected as shown below:

Column 10, line 25, should read--organic compound selected from the group consisting of 3,17 B-diacetoxy -3,5-androstadiene, 3,17 B-bistrimethyl-siloxy-3,5-androstadiene, and 3 B-acetoxy 17-acetamino-5,16-androstadiene --.

Signed and Sealed this

Twenty-fifth Day of May, 1993

Attest:

MICHAEL K. KIRK

*Attesting Officer*    *Acting Commissioner of Patents and Trademarks*